United States Patent [19]
Tso et al.

[11] Patent Number: 5,932,448
[45] Date of Patent: Aug. 3, 1999

[54] BISPECIFIC ANTIBODY HETERODIMERS

[75] Inventors: J. Yun Tso, Menlo Park; Sheri A. Kostelny, Mountain View; Michael S. Cole, Palo Alto, all of Calif.

[73] Assignee: Protein Design Labs., Inc., Mountain View, Calif.

[21] Appl. No.: 07/801,798

[22] Filed: Nov. 29, 1991

[51] Int. Cl.$^6$ ............... C12P 21/04; C12P 21/08; C07K 1/113; C07K 16/28

[52] U.S. Cl. .................... 435/69.6; 530/388.22; 530/388.75; 530/402; 530/387.3; 435/69.7; 435/70.21

[58] Field of Search ............... 530/387.3, 388.23, 530/388.75, 402, 388.22; 435/69.6, 69.7, 70.21

[56] References Cited

U.S. PATENT DOCUMENTS 5,582,996  12/1996  Curtis ............... 435/7.1

OTHER PUBLICATIONS

Abel and Maniatis, Nature 341:24–25 (1989).
Bator and Reading, in Therapeutic Monoclonal Antibodies, Borrebaech and Larrick, eds., Stockton Press, p. 35 (1990).
Better et al., Science 240:1041–1943 (1988).
Brennan et al., Science 229:81–83 (1985).
Gilliland et al., Proc. Natl. Acad. Sci. USA 85:7719–7723 (1988).
Blondel and Bedouelle, Protein Engineering 4:457–461 (1991).
Curran and Franza, Cell 55:395–397 (1988).
Glennie et al., J. Immunol. 139:2367–2375 (1987).
Landschulz et al., Science 240:1759–1764 (1988).
Lanzavecchia and Scheidegger, Eur. J. Immunol. 17:105–111 (1987).
McKnight, Scientific American, pp. 54–64, Apr. 1991.
Milstein and Cuello, Immunol. Today 5:299–304 (1984).
Neuberger et al., Nature 312:604–608 (1984).
O'Shea et al., Science 254:539–554 (1991).
O'Shea et al., Science 245:646–648 (1989).
Parham, J. Immunol. 131:2895–2902 (1983).
Queen et al., Proc. Natl. Acad. Sci. USA 86:10029–1033 (1989).
Shin and Morrison, Proc. Natl. Acad. Sci. USA 87:5322–5326 (1990).
Staerz and Bevan, Immunology Today 7:241–245 (1986).
Uchiyama et al., J. Immunol. 126:1393–1397 (1981).
Schuermann et. al. Feb. 1991 Nucleic Acids Research. vol. 19. No. 4, 739.

*Primary Examiner*—Lila Feisee
*Assistant Examiner*—Geetha Bansal
*Attorney, Agent, or Firm*—Townsend & Townsend & Crew

[57] ABSTRACT

Methods for producing and using bispecific antibodies formed by leucine zippers are provided. Leucine zippers capable of preferentially forming heterodimers are respectively linked to epitope binding components comprising different binding specificities. Bispecific antibodies are formed by pairwise association of the leucine zippers, forming a heterodimer which links the two distinct epitope binding components. Heterodimerization can occur by interaction of the two leucine zipper regions, forming a bispecific antibody. Such a bispecific antibody may be further stabilized by the formation of intermolecular chemical bonds, such as disulfide bonds, between the two monomeric subunits. Subsequent to the formation of such intermolecular bonds between the monomeric subunits, the leucine zippers may be removed or retained. Bispecific antibodies produced by these methods are substantially pure and may be produced in high yields and on a large scale. Alternatively, bifunctional heterodimers may be formed by linking an epitope binding component to a macromolecular species that is not an epitope binding component.

16 Claims, 8 Drawing Sheets

```
 1  CCATCTCTCCTCATCA  GCA  GGC  GGC  CGC  ATC  GCC  CGG  CTC  GAG  GAA
                   1- Ala  Gly  Gly  Arg  Ile  Ala  Arg  Leu  Glu  Glu
      H:CH2 INTRON   CH2           ├──────── JUN LEUCINE ZIPPER ────────
47  AAA  GTG  AAA  ACC  TTG  AAA  GCT  CAG  AAC  TCG  GAG  CTC  GCG  TCC
11- Lys  Val  Lys  Thr  Leu  Lys  Ala  Gln  Asn  Ser  Glu  Leu  Ala  Ser

89  ACG  GCC  AAC  ATG  CTC  AGG  GAA  CAG  GTG  GCA  CAG  CTT  AAA  CAG
25- Thr  Ala  Asn  Met  Leu  Arg  Glu  Gln  Val  Ala  Gln  Leu  Lys  Gln

SalI
131 AAA  GTC  ATG  AAC  TGA  GTCGAC
39- Lys  Val  Met  Asn  STOP
```

FIG. 1a.

```
 1  CCATCTCTCCTCATCA  GCA  GGC  GGG  TTA  ACT  GAT  ACA  CTC  CAA  GCG
                   1- Ala  Gly  Gly  Leu  Thr  Asp  Thr  Leu  Gln  Ala
      H:CH2 INTRON   CH2           ├──────── FOS LEUCINE ZIPPER ────────
47  GAG  ACC  GAC  CAG  CTG  GAA  GAT  AAG  AAG  TCT  GCT  CTG  CAG  ACC
11- Glu  Thr  Asp  Gln  Leu  Glu  Asp  Lys  Lys  Ser  Ala  Leu  Gln  Thr

89  GAG  ATT  GCC  AAC  CTG  CTG  AAG  GAG  AAG  GAA  AAA  CTG  GAG  TTC
25- Glu  Ile  Ala  Asn  Leu  Leu  Lys  Glu  Lys  Glu  Lys  Leu  Glu  Phe

SalI
131 ATC  CTG  GCC  GCC  TGA  GTCGAC
39- Ile  Leu  Ala  Ala  STOP
```

FIG. 1b.

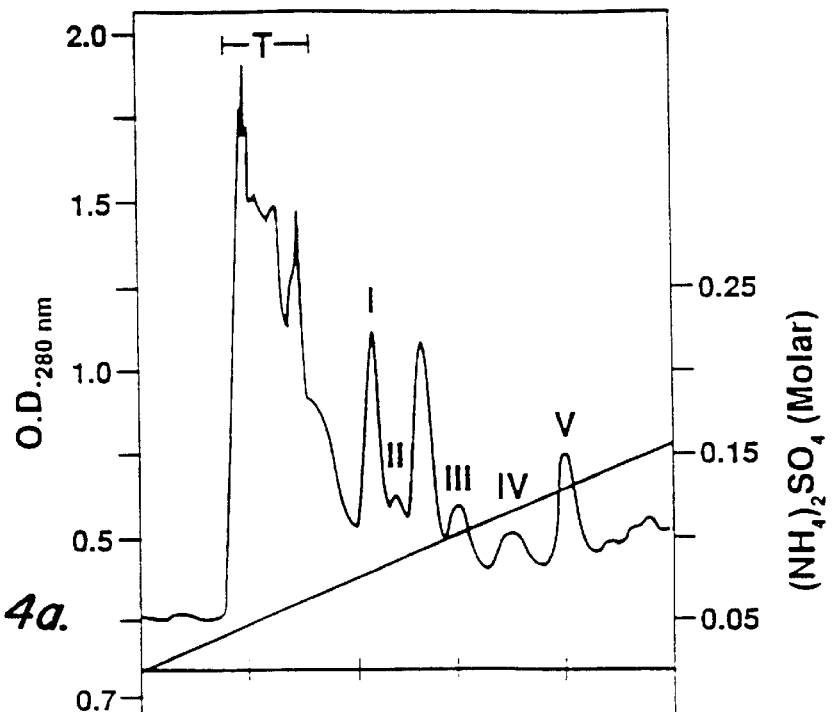
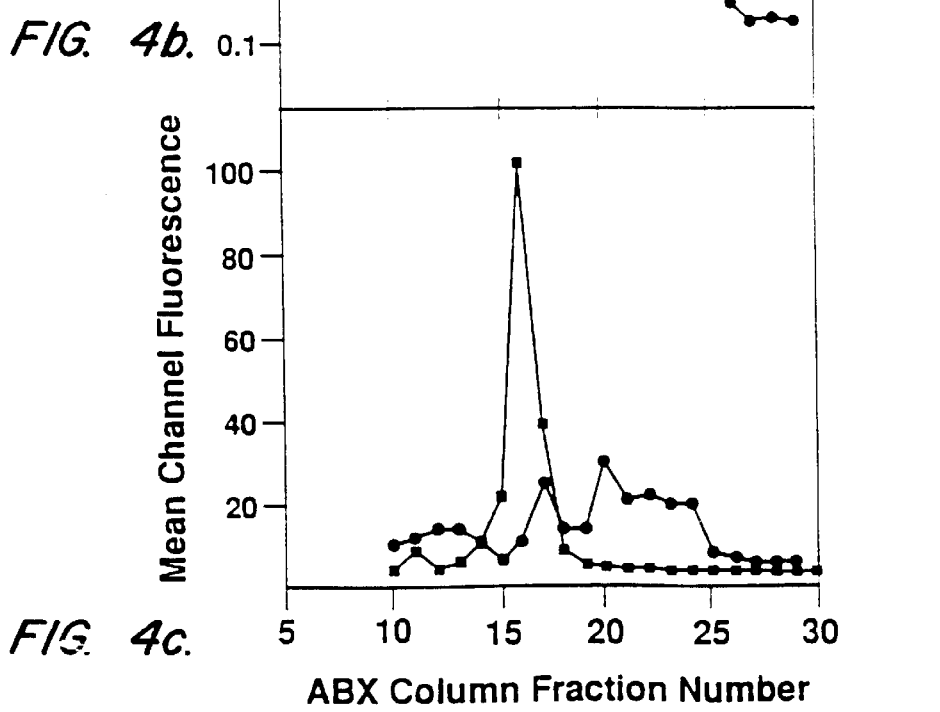
FIG. 4a.
FIG. 4b.
FIG. 4c.
ABX Column Fraction Number

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Region
      (B) LOCATION: 2..7
      (D) OTHER INFORMATION: /note= "Residues 2-7 can be any of
          the 20 naturally ocurring amino acids."

(xi) SEQUENCE DESCRIPTION: SEQ ID NO:1:

Leu Xaa Xaa Xaa Xaa Xaa Xaa
1            5

(2) INFORMATION FOR SEQ ID NO:2:

(i) SEQUENCE CHARACTERISTICS:
      (A) LENGTH: 151 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: intron
      (B) LOCATION: 1..16

(ix) FEATURE:
      (A) NAME/KEY: CDS
      (B) LOCATION: 17..143

(xi) SEQUENCE DESCRIPTION: SEQ ID NO:2:

```
CCATCTCTCC TCATCA GCA GGC GGC CGC ATC GCC CGG CTC GAG GAA AAA         49
                 Ala Gly Gly Arg Ile Ala Arg Leu Glu Glu Lys
                  1               5                  10
```

```
GTG AAA ACC TTG AAA GCT CAG AAC TCG GAG CTC GCG TCC ACG GCC AAC         97
Val Lys Thr Leu Lys Ala Gln Asn Ser Glu Leu Ala Ser Thr Ala Asn
         15                  20                  25

ATG CTC AGG GAA CAG GTG GCA CAG CTT AAA CAG AAA GTC ATG AAC T          143
Met Leu Arg Glu Gln Val Ala Gln Leu Lys Gln Lys Val Met Asn
     30                  35                  40

GAGTCGAC                                                                151
```

(2) INFORMATION FOR SEQ ID NO:3:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO:3:

```
Ala Gly Gly Arg Ile Ala Arg Leu Glu Glu Lys Val Lys Thr Leu Lys
 1               5                  10                  15

Ala Gln Asn Ser Glu Leu Ala Ser Thr Ala Asn Met Leu Arg Glu Gln
             20                  25                  30

Val Ala Gln Leu Lys Gln Lys Val Met Asn
             35                  40
```

(2) INFORMATION FOR SEQ ID NO:4:

(i) SEQUENCE CHARACTERISTICS:
        (A) LENGTH: 151 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: intron
        (B) LOCATION: 1..16

(ix) FEATURE:
        (A) NAME/KEY: CDS
        (B) LOCATION: 17..143

(xi) SEQUENCE DESCRIPTION: SEQ ID NO:4:

```
CCATCTCTCC TCATCA GCA GGC GGG TTA ACT GAT ACA CTC CAA GCG GAG           49
                Ala Gly Gly Leu Thr Asp Thr Leu Gln Ala Glu
                 1               5                  10

ACC GAC CAG CTG GAA GAT AAG AAG TCT GCT CTG CAG ACC GAG ATT GCC         97
Thr Asp Gln Leu Glu Asp Lys Lys Ser Ala Leu Gln Thr Glu Ile Ala
         15                  20                  25

AAC CTG CTG AAG GAG AAG GAA AAA CTG GAG TTC ATC CTG GCC GCC T          143
Asn Leu Leu Lys Glu Lys Glu Lys Leu Glu Phe Ile Leu Ala Ala
     30                  35                  40

GAGTCGAC                                                                151
```

(2) INFORMATION FOR SEQ ID NO:5:

(i) SEQUENCE CHARACTERISTICS:
        (A) LENGTH: 42 amino acids
        (B) TYPE: amino acid
        (D) TOPOLOGY: linear (ii) MOLECULE TYPE: protein (xi) SEQUENCE DESCRIPTION: SEQ ID NO:5:

```
Ala Gly Gly Leu Thr Asp Thr Leu Gln Ala Glu Thr Asp Gln Leu Glu
 1               5                  10                  15
```

```
Asp Lys Lys Ser Ala Leu Gln Thr Glu Ile Ala Asn Leu Leu Lys Glu
             20                  25                  30

Lys Glu Lys Leu Glu Phe Ile Leu Ala Ala
         35                  40
```

BISPECIFIC ANTIBODY HETERODIMERS

TECHNICAL FIELD OF THE INVENTION

The invention relates to bispecific antibodies, epitope binding components capable of forming specific heterodimers with other epitope binding components, methods for producing such bispecific antibodies and epitope binding components, methods for using such bispecific antibodies and epitope binding components, and pharmaceutical compositions containing such bispecific antibodies and epitope binding components.

BACKGROUND OF THE INVENTION

Bispecific antibodies are antibodies with dual epitope binding specificities, with one specificity being the capacity to bind a first epitope and a second specificity being the capacity to bind a second epitope.

Such bispecific antibodies are, in some embodiments, potentially valuable molecules for immunotherapy. For example, bispecific antibodies can crosslink cytotoxic effector cells to target cells (Segal and Snider, (1989) *Chem. Immunol.* 47:179), resulting in the killing of the target cell.

Although numerous bispecific antibodies have been shown effective in vitro (Gililand et al., (1988) *Proc. Natl. Acad. Sci. USA* 85:7719; Lanzavecchia and Scheidegger, (1987) *Eur. J. Immunol.* 17:105; Stearz and Bevan, (1986) *Immunol. Today* 7:241; Berg et al., (1991) *Proc. Natl. Acad. Sci. USA* 88:4732), few have been tested clinically as therapeutic agents. One of the reasons for the slow development of bispecific antibodies as therapeutic agents has been the difficulty in manufacturing them in sufficient purity and quantity.

Bispecific antibodies have been produced by chemical cross-linking, by hybrid-hybridomas (Milstein and Cuello, (1984) *Immunol. Today* 5:299) or transfectomas, or by disulfide exchange at the hinge of two different Fab'. The first method yields heterogeneous and ill-defined products. The second method requires extensive purification of the bispecific antibodies from many hybrid-antibody side products, the presence of which may interfere with the cell cross-linking activity. The disulfide exchange method applies essentially only to F(ab')$_2$, and is thus limited by the susceptibility of the monoclonal antibodies to cleavage by enzyme digestion (Parham, (1983) *J. Immunol.* 131:2895). Further, since Fab' have little affinity for each other, very high protein concentrations are required for the formation of the inter-Fab' disulfide bonds. The disulfide exchange method has been improved by the use of Ellman's reagent to modify one of the Fab' prior to oxidation with the other Fab', reducing the incidence of homodimerization (Brennan et al., (1985) *Science* 229:81). However, even with this improvement, heterodimeric F(ab')$_2$ can rarely be produced in better than 50% yield (Glennie et al., (1987) *J. Immunol.* 139:2367).

Thus, there remains a significant need for improved methods for efficiently producing bispecific antibodies and other similar compounds at high purity.

SUMMARY OF THE INVENTION

The present invention includes novel methods for the production of bispecific antibodies that include: 1) producing F(ab')$_2$ and/or other epitope binding components directly, e.g., by gene expression, and 2) utilizing heterodimer-forming sequences to ensure efficient production of the bispecific antibodies. The sequences employed may be derived from the leucine zipper (Landschulz et al., (1988) *Science* 240:1759, and for review, see Maniatis and Abel, (1989) *Nature* 341:24, both of which are incorporated herein by reference) regions of the transcription factors Fos and Jun. Leucine zippers are specific amino acid sequences about 20–40 residues long with leucine typically occurring at every seventh residue. Such zipper sequences form amphipathic α-helices, with the leucine residues lined up on the hydrophobic side for dimer formation. Peptides corresponding to the leucine zippers of the Fos and Jun proteins form heterodimers preferentially (O'Shea et al. (1989) *Science* 245:646).

In the present invention, two leucine zipper sequences are employed to promote bispecific F(ab')$_2$ formation when fused to two different Fab'. Bispecific antibodies are produced by the methods of the invention, whereby the pairwise association of two distinct zipper sequences links a first Fab' or other epitope binding component containing one zipper to a second Fab' or other epitope binding component that contains the other zipper. In these embodiments, a heterodimeric molecule will comprise the binding properties of both epitope binding components.

The present invention provides bispecific antibodies formed from a first protein which includes a leucine zipper linked to an epitope binding component and a second protein which includes a leucine zipper linked to an epitope binding component, wherein the leucine zippers of the first and second proteins have pairwise affinity so that heterodimers comprising the first and second proteins are formed. In some embodiments of the invention, one of the leucine zippers is a Fos leucine zipper or a Jun leucine zipper. In one embodiment of the invention, one leucine zipper is a Fos leucine zipper and the other leucine zipper is a Jun leucine zipper. The invention also provides bispecific antibodies which have a first and second leucine zipper of the structural sequence (leucine-$X_1$-$X_2$-$X_3$-$X_4$-$X_5$-$X_6$)$_n$ (SEQ ID NO: 1), wherein each of $X_1$, $X_2$, $X_3$, $X_4$, $X_5$, and $X_6$ is one of the conventional 20 amino acids and n is an integer that is at least 3.

The present invention provides bispecific antibodies which bind to a human IL-2 receptor and bispecific antibodies which bind to a human CD3 protein. The present invention also provides bispecific antibodies that have at least one epitope binding component that is an Fab'. Some embodiments of the present invention have at least one epitope binding component that is a humanized immunoglobulin.

The present invention also provides methods for preparing bispecific antibodies where a first and a second protein are produced, each including an epitope binding component and a leucine zipper, and the first and second proteins are contacted under conditions that permit heterodimer formation to form a bispecific antibody. The contacting of the first and second proteins may occur in vitro or in vivo in a single cell that expresses both proteins. In some embodiments, the methods employ proteins that have a Fos or Jun leucine zipper or other similar leucine zippers corresponding to the formula (leucine-$X_1$-$X_2$-$X_3$-$X_4$-$X_5$-$X_6$)$_n$, wherein each of $X_1$, $X_2$, $X_3$, $X_4$, $X_5$, and $X_6$ is one of the conventional 20 amino acids and n is an integer that is at least 3. In some methods of the invention, the F(ab'-zipper)$_2$ heterodimer bispecific antibody may be produced as a final product, or it may be cleaved (e.g., cleavage of an asparagine-glycine peptide bond by hydroxylamine) to remove the leucine zippers to yield a F(ab')$_2$ bispecific antibody wherein the two Fab' are chemically linked (e.g., by a disulfide bond). Epitope binding components other than Fab' may be used in methods of the present invention to form bispecific antibodies which are linked by a chemical bond but which have had the leucine zippers removed.

The present invention also provides polynucleotides that encode proteins that include an epitope binding component and a leucine zipper, particularly including an epitope binding component that has the V, $C_{H1}$, and hinge domains of an antibody heavy chain, and more particularly a Fab'.

Other bispecific antibodies, wherein epitope binding components other than Fab' are used, and/or wherein one component of the bispecific antibody is a macromolecular species that is not an epitope binding component, can also be generated by these methods.

The present invention also encompasses pharmaceutical compositions of bispecific antibodies, therapeutic uses of such bispecific antibodies, methods and compositions for using bispecific antibodies in diagnostic and research applications.

BRIEF DESCRIPTION OF THE DRAWINGS

FIG. 1. Sequences containing the Jun (A) (SEQ. ID NOS:2 and 3) and Fos (B) (SEQ. ID NOS:4 and 5) leucine zipper. Arrows indicate the splicing sites between intron H:$C_H2$ and exon $C_H2$.

FIG. 4. Fractionation of the spent medium of the anti-Tac-Jun and anti-CD3-Fos expressing supertransfectant on BAKERBOND ABx column by FPLC. (A) Absorbance profile of proteins at 280 nm as they were eluted by a gradient of $(NH_4)_2SO_4$. Proteins that were eluted early (fraction T) are mostly medium supplements such as transferrin and insulin. (B) Mouse IgG positive fractions as determined by ELISA. Absorbance at 414 nm represents the color developed by the secondary antibodies, which were peroxidase-conjugated goat anti-mouse IgG. (C) Anti-CD3 (●) and anti-Tac (■) activities for different fractions assayed by flow cytometry.

FIG. 9. Targeted cytotoxicity mediated by bispecific anti-Tac-Jun x anti-CD3-Fos formed in vitro. Effectors and $^{51}$Cr-labeled target cells at a ratio of 25:1 (○) and 10:1 (●) were incubated with various concentrations of fraction III (FIG. 7A) for specific lysis.

DETAILED DESCRIPTION OF THE INVENTION

Figure 2A:
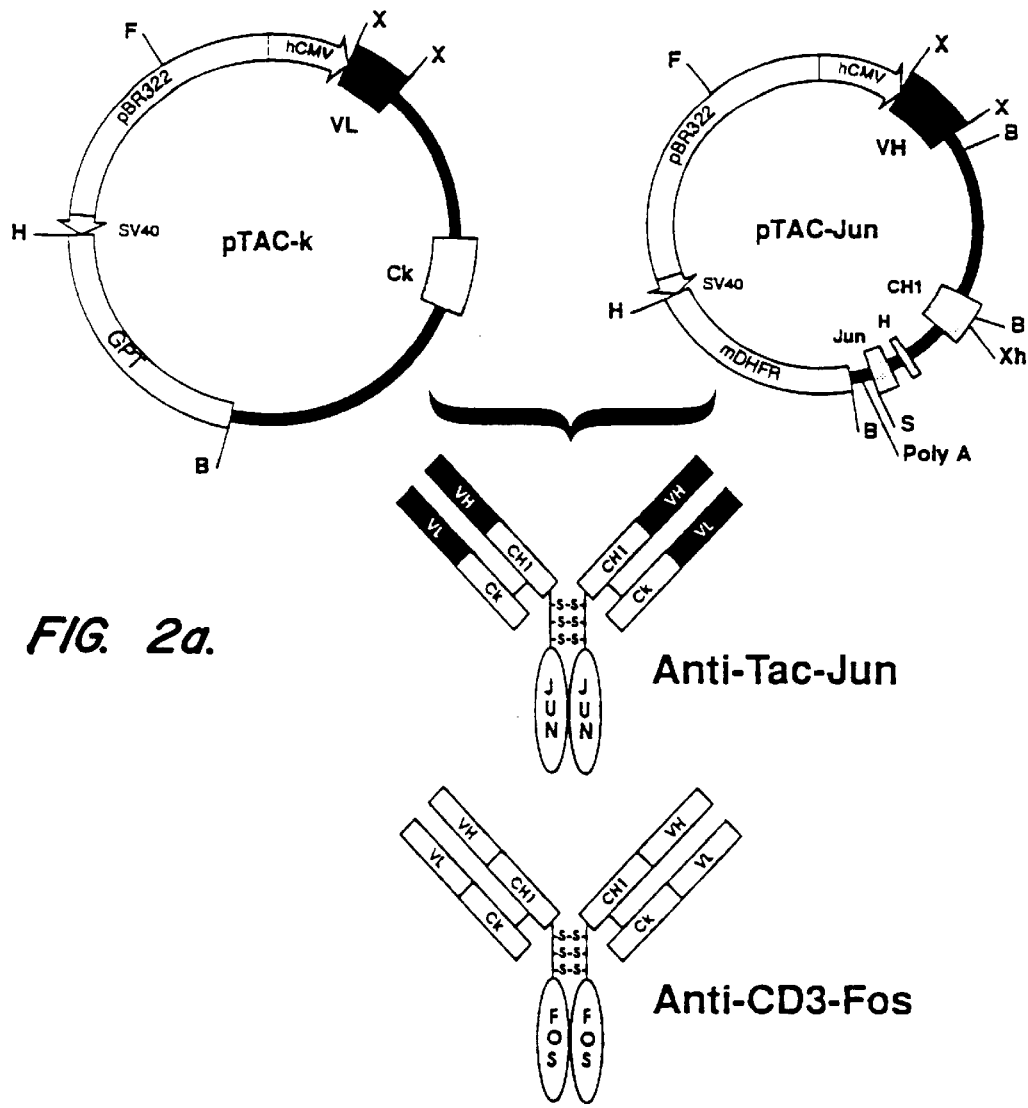
FIG. 2. Diagrams of plasmid constructs for expression of anti-Tac-Jun (A) and anti-CD3-Fos (B). Schematic diagrams of the protein products are also shown. Coding sequences are shown as boxes. Symbols for restriction sites are: B, BamHI; F, FspI; H, HindIII; S, SalI; X, XbaI; and Xh, XhoI.

In accordance with the present invention, bispecific antibodies, methods to produce such bispecific antibodies, pharmaceutical compositions of bispecific antibodies, therapeutic uses of such bispecific antibodies, and methods and compositions for using bispecific antibodies in diagnostic and research applications are provided.

Definitions

"F(ab')$_2$ heterodimer" is defined herein as a dimer comprising a first Fab' having a binding specificity for a first epitope, and a second Fab' having a binding specificity for a second epitope, wherein the first and second epitopes are nonidentical.

"Fab'-zipper" is defined as an Fab' linked to a leucine zipper.

"F(ab'-zipper)$_2$ heterodimer" is defined herein as a dimer comprising a first Fab' having a binding specificity for a first epitope and linked to a leucine zipper, and a second Fab' having a binding specificity for a second epitope and linked to a leucine zipper, wherein said first and second epitopes are nonidentical.

"Epitope binding components" of the present invention refer to proteins consisting of one or more polypeptides substantially encoded by genes of the immunoglobulin superfamily (e.g., see *The Immunoglobulin Gene Superfamily*, A. F. Williams and A. N. Barclay, in *Immunoglobulin Genes*, T. Honjo, F. W. Alt, and T. H. Rabbitts, eds., (1989) Academic Press: San Diego, Calif., pp.361–387, which is incorporated herein by reference). For example, but not for limitation, an epitope binding component may comprise part or all of a heavy chain and part or all of a light chain, or may comprise only part or all of a heavy chain. However, an epitope binding component must contain a sufficient portion of at an immunoglobulin superfamily gene product so as to retain the property of binding to a specific target, or epitope.

Leucine zipper

Recently, a protein structural motif designated as a "leucine zipper" has been identified (Landschulz et al., (1988) *Science* 240:1759). The leucine zipper has been defined in the art as a stretch of about 35 amino acids containing 4–5 leucine residues separated from each other by six amino acids (Maniatis and Abel, (1989) *Nature* 341:24). The leucine zipper has been found to occur in a variety of eukaryotic DNA-binding proteins, such as GCN4, C/EBP, c-fos gene product (Fos), c-jun gene product (Jun), and c-myc gene product. In these proteins, the leucine zipper creates a dimerization interface wherein proteins containing leucine zippers may form stable homodimers and/or heterodimers.

Molecular analysis of the protein products encoded by two proto-oncogenes, c-fos and c-jun, has revealed such a case of preferential heterodimer formation. Both of these DNA-binding proteins contain leucine zipper regions, however while Jun is capable of forming a homodimer, and Fos and Jun are capable of heterodimerizing with each other, there has been little evidence for the homodimerization of Fos (Gentz et al., (1989) *Science* 243:1695; Nakabeppu et al., (1988) *Cell* 55:907; Cohen et al., (1989) *Genes Dev.* 3:173). Thus, the Fos leucine zipper is able to preferentially dimerize with Jun because of a characteristic interaction at the helix interface between the Jun leucine zipper and the Fos leucine zipper (O'Shea et al. *op.cit.*; Schuemann et al., (1991) *Nucleic Acids Res.* 19:739).

Synthetic peptides comprising the leucine zipper regions of Fos and Jun are sufficient by themselves to mediate heterodimer formation, and, where the amino-termini of the synthetic peptides each include a cysteine residue to permit intermolecular disulfide bonding, heterodimer formation occurs to the substantial exclusion of homodimerization.

Leucine zippers of the present invention have the general structural formula known as the heptad repeat (Leucine-$X_1$-$X_2$-$X_3$-$X_4$-$X_5$-$X_6$)$_n$, where X may be any of the conventional 20 amino acids (*Proteins, Structures and Molecular Principles*, (1984) Creighton (ed.), W. H. Freeman and Company, New York, which is incorporated herein by reference), but are most likely to be amino acids with high α-helix forming potential, for example, alanine, valine, aspartic acid, glutamic acid, and lysine (Richardson and Richardson, (1988) *Science* 240:1648), and n may be 3 or greater, although typically n is 4 or 5. The 20 conventional amino acids are: glycine, proline, lysine, arginine, histidine, methionine, tryptophan, phenylalanine, isoleucine, leucine, valine, alanine, serine, threonine, cysteine, glutamine, asparagine, tyrosine, aspartic acid, and glutamic acid.

The leucine zippers of the present invention have pairwise affinity. Leucine zippers form amphipathic alpha helices, and more specifically form coiled coils. Pairwise affinity is defined as the capacity for one specie of leucine zipper, for example but not for limitation, the Fos leucine zipper, to predominantly form heterodimers with another specie of leucine zipper, for example but not for limitation, the Jun leucine zipper, such that heterodimer formation is preferred over homodimer formation when two species of leucine zipper are present in sufficient concentrations. Thus, predominant formation of heterodimers leads to a dimer population that is typically 50 to 75 percent, preferentially 75 to 85 percent, and most preferably more than 85 percent heterodimers. "Fos Leucine zipper" is defined as a sequence of amino acids substantially similar to the sequence shown in FIG. 1(*b*). "Jun leucine zipper" is defined as a sequence of amino acids substantially similar to the sequence shown in FIG. 1(*a*). Those of skill in the art will understand that leucine zippers of the present invention may comprise amino acids sequences that are not identical to those shown in FIG. 1, by, for example but not for limitation, having internal or terminal additions, deletions, or substitutions, or by having rearrangement of the order of the heptad repeats. For illustration, but not for limitation, the invention encompasses additions or substitutions of terminal amino acids that comprise glycine and/or cysteine.

The leucine zipper regions of the Jun and Fos proteins normally serve to bind the proteins together to form a transcription factor, AP-1. The Jun and Fos zippers will also dimerize other proteins to which they have been genetically fused, such as two Fab' halves of a bispecific antibody. Because the pairwise association of the two zipper peptides results in a much greater tendency to form heterodimers than homodimers, formation of the desired product is enhanced.

Bispecific antibodies

Bispecific antibodies can be formed by joining two epitope binding components that have different binding specificities.

"Epitope binding components" of the present invention refer to a protein consisting of one or more polypeptides substantially encoded by immunoglobulin superfamily genes and having specific binding affinity for an epitope of an antigen. The recognized immunoglobulin gene superfamily is described in *The Immunoglobulin Gene Superfamily*, A. F. Williams and A. N. Barclay, op. cite). Specific examples of immunoglobulin genes include the kappa, lambda, alpha, gamma, delta, epsilon and mu constant region genes, as well as the myriad immunoglobulin variable region genes. The immunoglobulins may exist in a variety of forms besides antibodies; including, for example, Fv, Fab, and F(ab)$_2$, as well as in single chains (e.g., Huston, et al., *Proc. Nat. Acad. Sci. U.S.A.*, 85:5879–5883 (1988) and Bird, et al., *Science*, 242:423–426 (1988), which are incorporated herein by reference). (See, generally, Hood, et al., "Immunology", Benjamin, N.Y., 2nd ed. (1984), and Hunkapiller and Hood, *Nature*, 323:15–16 (1986), which are incorporated herein by reference). Other examples of epitope binding components include T-cell antigen receptors and the CD4 protein, which binds to an epitope on MHC protein.

It is well known that native forms of "mature" immunoglobulins will vary somewhat in terms of length by deletions, substitutions, insertions or additions of one or more amino acids in the sequences. Thus, both the variable and constant regions are subject to substantial natural modification, yet are "substantially identical" and still capable of retaining their respective activities. Human constant region and rearranged variable region DNA sequences can be isolated in accordance with well known procedures from a variety of human cells, but preferably immortalized B-cells. Similar methods can be used to isolate nonhuman immunoglobulin sequences from non-human sources. Suitable source cells for the DNA sequences and host cells for expression and secretion can be obtained from a number of sources, such as the American Type Culture Collection ("Catalogue of Cell Lines and Hybridomas," Fifth edition (1985) Rockville, Md., U.S.A., which is incorporated herein by reference).

In addition to these naturally-occurring forms of immunoglobulin chains, "substantially identical" modified heavy and light chains can be readily designed and manufactured utilizing various recombinant DNA techniques well known to those skilled in the art. For example, the chains can vary from the naturally-occurring sequence at the primary structure level by several amino acid substitutions, terminal and intermediate additions and deletions, and the like.

Alternatively, polypeptide fragments comprising only a portion of the primary structure may be produced, which fragments possess one or more immunoglobulin activities (e.g., binding activity). In particular, it is noted that like many genes, the immunoglobulin-related genes contain separate functional regions, each having one or more distinct biological activities. In general, modifications of the genes encoding the desired epitope binding components may be readily accomplished by a variety of well-known techniques, such as site-directed mutagenesis (see, Gillman and Smith, *Gene* 8:81–97 (1979) and Roberts, S. et al., *Nature* 328:731–734 (1987), both of which are incorporated herein by reference). In preferred embodiments of the invention, the epitope binding component is encoded by immunoglobulin genes that are "chimeric" or "humanized" (see, generally, Co and Queen (1991) *Nature* 351:501, which is incorporated herein by reference).

Suitable epitope binding components may be produced by those of skill in the art from DNA sequences or monoclonal antibody sources well-known in the art, and described with more particularity in W090/07861 and U.S. Ser. No. 07/310,252, which are incorporated herein by reference.

The Fab'-Jun (Fab' containing a Jun leucine zipper) and Fab'-Fos (Fab' containing a Fos leucine zipper) proteins can be used to produce bispecific antibodies either in vivo, by coexpression in one cell line, or by mixing in vitro after expression in separate cells. The in vitro mixing procedure is preferred for large-scale production of bispecific antibodies. In addition to Fab', other epitope binding components may be linked to a Jun or Fos leucine zipper, and combined by in vitro mixing.

The in vitro mixing procedure has the advantage that a particular Fab'-Fos or Fab'-Jun need only be generated once, as it can then be combined with a variety of epitope binding components that contain the complementary leucine zipper. For example, the T cell binding component of a bispecific antibody, an Fab' comprising a Fos leucine zipper and a binding specificity for the T cell antigen CD3, need only be generated once, as it can then be combined with any one of a variety of epitope binding components that contain the Jun leucine zipper, such as an Fab'-Jun molecule that has a binding affinity for a desired target cell. In addition, Fab fragments have been produced in *Esherichia coli* at high levels, so that the F(ab'-zipper)$_2$ bispecific antibodies may also potentially be produced economically in large quantity, making clinical trials possible.

Leucine zippers linked to epitope binding components may be produced in various ways. For example but not limitation, polynucleotide sequences encoding a fusion protein comprising a leucine zipper may be expressed by a cellular host or in vitro translation system. Alternatively, leucine zippers and/or epitope binding components may be produced separately, either by chemical peptide synthesis, by expression of polynucleotide sequences encoding the desired polypeptides, or by cleavage from other proteins containing leucine zippers, antibodies, or macromolecular species, and subsequent purification. Such purified polypeptides may be linked by peptide bonds, with or without intervening spacer amino acid sequences, or by non-peptide covalent bonds, with or without intervening spacer molecules, said spacer molecules being either amino acids or other non-amino acid chemical structures. Regardless of the method or type of linkage, such linkage may be reversible. For example but not limitation, such reversible linkage may comprise a chemically labile bond, either peptidyl or otherwise, which may be cleaved spontaneously or upon treatment with heat, electromagnetic radiation, proteases, or chemical agents. Two examples of such reversible linkage are offered for illustration and not for limitation, they are: (1) a linkage comprising a Asn-Gly peptide bond which can be cleaved by hydroxylamine, and (2) a disulfide bond linkage which can be cleaved by reducing agents.

Generally, the nomenclature used hereafter and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., 1989. Other general references are provided throughout this document. The procedures therein are believed to be well known in the art and are provided for the convenience of the reader. All the information contained therein is incorporated herein by reference.

The nucleic acid sequences of the present invention capable of ultimately expressing the desired bispecific antibodies can be formed from a variety of different polynucleotides (genomic or cDNA, RNA, etc.) by a variety of different techniques. Joining appropriate genomic sequences is presently the most common method of production, but cDNA and synthetic sequences may also be utilized (see, European Patent Application Nos. 85102655.8, 85305604.2, 84302368.0 and 85115311.4, as well as PCT Application Nos. GB85/00392 and U.S. Ser. No. 86/02269, all of which are incorporated herein by reference).

The DNA constructs will typically include an expression control DNA sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions-suitable for high level expression of the nucleotide sequences, and the collection and purification of the bispecific antibodies.

As stated previously, the DNA sequences will be expressed in hosts after the sequences have been operably linked to an expression control sequence (i.e., positioned to ensure the translation of the structural gene). These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

In general, prokaryotes can be used for cloning the DNA sequences encoding the components of bispecific antibodies. *E. coli* is one prokaryotic host particularly useful for cloning the DNA sequences of the present invention. Particular *E. coli* strains that can be used include, HB101, DH-1, and MH-1.

Other microbial hosts suitable for use include bacilli, such as *Bacillus subtilus*, and other enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast may also be used for expression. Saccharomyces is a preferred host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase 2, isocytochrome C, and enzymes responsible for maltose and galactose utilization.

When constructing vectors for use in yeast, the plasmid YRp7 can be used (see, Stinchcomb, et al., *Nature*, 282: 39 (1979)). This plasmid contains the trp1 gene which is a selectable marker for a mutant strain which lacks the ability to grow on media containing tryptophan. The presence of the trp1 gene allows transformed mutant cells to grow on selective media and to be identified.

In addition to microorganisms, mammalian tissue cell culture may also be used to produce the polypeptides of the present invention (see, Winnacker, "From Genes to Clones," VCH Publishers, N.Y., N.Y. (1987), which is incorporated herein by reference). Eukaryotic cells are actually preferred, because a number of suitable host cell lines capable of secreting intact immunoglobulins have been developed in the art, and include the CHO cell lines, various COS cell lines, HeLa cells, myeloma cell lines, etc, but preferably transformed B-cells or hybridomas. Expression vectors for these cells can include expression control sequences, such as an origin of replication, a promoter, an enhancer (Queen, C. et al., *Immunol. Rev.* 89:49–68 (1986), which is incorporated herein by reference), and necessary processing information sites, such as ribosome binding sites, RNA splice sites, polyadenylation sites, and transcriptional terminator sequences. Preferred expression control sequences are promoters derived from immunoglobulin genes, cytomegalovirus, SV40, Adenovirus, Bovine Papilloma Virus, and the like.

Eukaryotic DNA transcription can be increased by inserting an enhancer sequence into the vector. Enhancers are cis-acting sequences of between 10 to 300 bp that increase transcription by a promoter. Enhancers can effectively increase transcription when either 5' or 3' to the transcription unit. They are also effective if located within an intron or within the coding sequence itself. Typically, viral enhancers are used, including SV40 enhancers, cytomegalovirus enhancers, polyoma enhancers, and adenovirus enhancers. Enhancer sequences from mammalian systems are also commonly used, such as the mouse immunoglobulin heavy chain enhancer.

Mammalian expression vector systems will also typically include a selectable marker gene. Examples of suitable markers include, the dihydrofolate reductase gene (DHFR), the thymidine kinase gene (TK), or prokaryotic genes conferring drug resistance. The first two marker genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to G418, mycophenolic acid and hygromycin.

The vectors containing the DNA segments of interest can be transferred into the host cell by well-known methods, depending on the type of cellular host. For example, calcium chloride transfection is commonly utilized for prokaryotic cells, whereas calcium phosphate treatment or electroporation may be used for other cellular hosts. Other methods used to transform mammalian cells include the use of Polybrene, protoplast fusion, liposomes and microinjection (see, generally, Sambrook et al., supra).

Once expressed, bispecific antibodies, epitope binding components, their dimers, or individual light and heavy chains with or without linked leucine zippers, or individual leucine zipper species themselves can be purified according to standard procedures of the art, including ammonium sulfate precipitation, fraction column chromatography, gel electrophoresis and the like (see, generally, Scopes, R., *Protein Purification*, Springer-Verlag, N.Y. (1982)). Once purified, partially or to homogeneity as desired, the polypeptides may then be used therapeutically or in developing and performing assay procedures, immunofluorescent stainings, and the like (see, generally, *Immunological Methods*, Vols. I and II, Eds. Lefkovits and Pernis, Academic Press, New York, N.Y. (1979 and 1981)).

The bispecific antibodies of the present invention can be used for therapy. By way of illustration and not limitation, they can be used to treat cancer, autoimmune diseases, or viral infections. For treatment of cancer, one of the epitope binding components will typically bind to an antigen expressed preferentially on cancer cells, such as erbB-2, CEA, CD33, and many other antigens well known to those skilled in the art. For treatment of autoimmune disease, one of the epitope binding components will typically bind to an antigen expressed on T-cells, such as CD4, the IL-2 receptor, the various T-cell antigen receptors and many other antigens well known to those skilled in the art (e.g., see *Fundamental Immunology*, 2nd ed., W. E. Paul, ed., Raven Press: New York, N.Y., which is incorporated herein by reference). For treatment of viral infections, one of the epitope binding components will typically bind to an antigen expressed on cells infected by a particular virus such as the various glycoproteins (e.g., gB, gD, gH) of herpes simplex virus and cytomegalovirus, and many other antigens well known to those skilled in the art (e.g., see *Virology*, 2nd ed., B. N. Fields et al., eds., (1990), Raven Press: New York, N.Y., which is incorporated herein by reference). In any case, the second epitope binding component will typically bind to an epitope expressed on T cells or other white blood cells that is capable of transmitting an activating signal, such as CD3 or CD16.

Pharmaceutical compositions comprising bispecific antibodies of the present invention are useful for parenteral administration, i.e., subcutaneously, intramuscularly or intravenously. The compositions for parenteral administration will commonly comprise a solution of the antibody or a cocktail thereof dissolved in an acceptable carrier, preferably an aqueous carrier. A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of the bispecific antibodies in these formulations can vary widely, i.e., from less than about 0.01%, usually at least about 0.1% to as much as 5% by weight and will be selected primarily based on fluid volumes, viscosities, etc., in accordance with the particular mode of administration selected.

Thus, a typical pharmaceutical composition for intramuscular injection could be made up to contain 1 ml sterile buffered water, and about 1 mg of bispecific antibody. A typical composition for intravenous infusion can be made up to contain 250 ml of sterile Ringer's solution, and 10 mg of bispecific antibody. Actual methods for preparing parenterally administrable compositions will be known or apparent to those skilled in the art and are described in more detail in, for example, *Remington's Pharmaceutical Science*, 15th Ed., Mack Publishing Company, Easton, Pa. (1980), which is incorporated herein by reference.

The bispecific antibodies of this invention can be lyophilized for storage and reconstituted in a suitable carrier prior to use. This technique has been shown to be effective with conventional immune globulins and art-known lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

The compositions containing the present bispecific antibodies or a cocktail thereof can be administered for prophylactic and/or therapeutic treatments. In therapeutic application, compositions are administered to a patient already affected by the particular disease, in an amount sufficient to cure or at least partially arrest the condition and its complications. An amount adequate to accomplish this is defined as a "therapeutically effective dose." Amounts effective for this use will depend upon the severity of the condition and the general state of the patient's own immune system, but generally range from about 0.01 to about 100 mg of bispecific antibody per dose, with dosages of from 1 to 10 mg per patient being more commonly used.

In prophylactic applications, compositions containing the bispecific antibodies or a cocktail thereof are administered to a patient not already in a disease state to enhance the patient's resistance. Such an amount is defined to be a "prophylactically effective dose." In this use, the precise amounts again depend upon the patient's state of health and general level of immunity, but generally range from 0.1 to 100 mg per dose, especially 1 to 10 mg per patient.

Single or multiple administrations of the compositions can be carried out with dose levels and pattern being selected by the treating physician. In any event, the pharmaceutical formulations should provide a quantity of the bispecific antibodies of this invention sufficient to effectively treat the patient.

The bispecific antibodies described herein can also be used to cross-link an epitope binding component and a detection agent such as ferritin (Hammerling et al., (1968) *J. Exp. Med.* 128: 1461) or horseradish peroxidase (Milstein and Cuello, (1983), *Nature* 305: 537) for diagnosis and imaging purposes. The detection agent can be linked to an epitope binding component through the second epitope binding component of the bispecific antibody, or be linked directly to the first epitope binding component by the heterodimer forming leucine zippers described herein. Similarly, metallothionein, a protein that binds heavy metal atoms, can be expresed with Fos leucine zipper as fusion protein and linked to Fab'-Jun. The resulting product can be used to deliver radionuclides to the antigen bearing site for imaging and therapy. Similarly, by way of example and not limitation, a protein toxin such as ricin or Pseudomonas aeruginosa exotoxin can also be fused with a Fos leucine zipper and then linked to a Fab'-Jun to be used as an immunotoxin.

Kits can also be supplied for use with the subject bispecific antibodies in the protection against or detection of a cellular activity or for the presence of a selected cell surface receptor. Thus, the subject composition of the present invention may be provided, usually in a lyophilized form in a container, either alone or in conjunction with additional antibodies specific for the desired cell type. The bispecific antibodies, which may be conjugated to a label or toxin, or unconjugated, are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1 to 99% wt. of the total composition. Where a second antibody capable of binding to the bispecific antibody is employed in an assay, this will usually be present in a separate vial. The second antibody is typically conjugated to a label and formulated in an analogous manner with the antibody formulations described above.

The following examples are offered by way of illustration, not by way of limitation.

EXPERIMENTAL

Figure 2B:
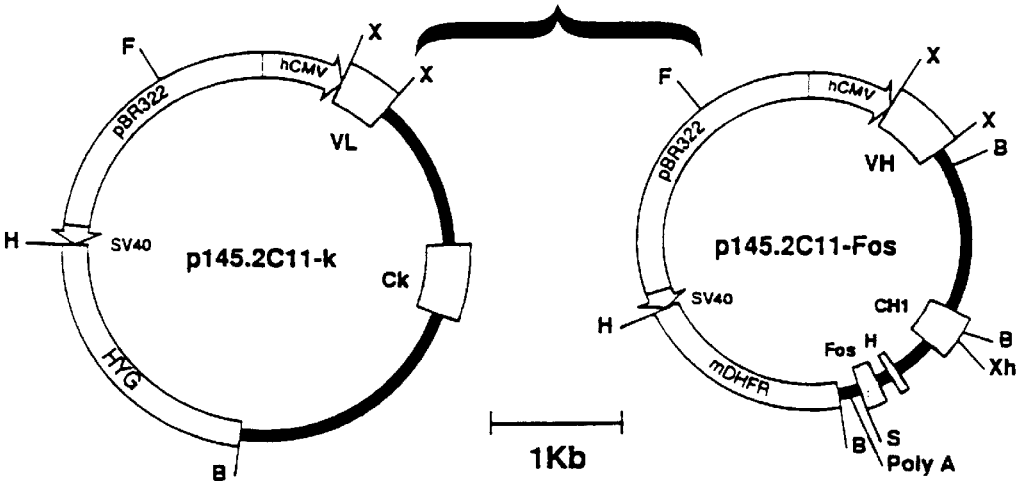

Construction of plasmids. Genes for the leucine zipper portions of Fos and Jun were separately synthesized, using four overlapping synthetic oligonucleotides (model 380B DNA synthesizer, Applied Biosystems, Foster City, Calif.). Each of the genes was then fused in phase to the first codon of the $C_H2$ exon of the mouse IgG2a gene (FIG. 1) using the polymerase chain reaction (PCR) method (Saiki et al., (1988) *Science* 239:487) described by Yon and Fried (Yon and Fried, (1989) *Nucl. Acid Res.* 17:4849). The resulting PCR products were 911 bp XhoI-SalI fragments, encompassing part of the $C_H1$ exon, the $C_H1$:H intron, the hinge (H) exon, the H:$C_H2$ intron, and the $C_H2$/zipper exon. The XhoI site is the natural restriction site within the $C_H1$ exon, but the SalI site was added to the end of the zipper sequences during PCR. A 162 bp SalI-BamHI fragment containing the 3' noncoding sequence of the mouse IgG2a gene was also generated by PCR. This sequence begins immediately 3' to the stop codon of the $C_H3$ exon and provides the polyadenylation signal. For the Jun and Fos constructs, the XhoI-SalI and the SalI-BamHI fragments were then inserted together between the XhoI and BamHI sites of a mouse heavy chain expression vector, replacing the $C_H2$ and the $C_H3$ exons with the $C_H2$/zipper exon (FIG. 2). The heavy chain expression vector, which contains the mutant dihydrofolate reductase gene (mdhfr) as the selectable marker (Simonsen and Levinson, (1983) *Proc. Natl. Acad. Sci. USA* 80:2495), the human cytomegalovirus (hCMV) major immediate early promoter and enhancer for transcription initiation (Boshart et al., (1985) *Cell* 41:521), and the mouse IgG2a constant region, was constructed from the respective fragments by standard methods.

A XbaI fragment containing the $V_H$ exon of the mouse anti-Tac heavy chain gene (Queen et al., (1989) *Proc. Natl. Acad. Sci. USA* 86:10029) was then inserted into the XbaI site of the Jun zipper containing vector (FIG. 2) to produce plasmid pTAC-Jun. Similarly, the $V_H$ gene of the hamster antibody 145-2C11 heavy chain gene was inserted in the Fos zipper containing vector to produce plasmid p145-2C11-Fos. For light chain expression, two vectors were used that contain the hCMV promoter and enhancer and the murine $C_k$ gene including part of the preceding intron. One of these vectors incorporates the xanthine-guanine phosphoribosyl transferase (gpt) gene (Mulligan and Berg, (1981) *Proc. Natl. Acad. Sci. USA* 78:2072) and the other the hygromycin B phosphotransferase (hyg) gene (Blochlinger and Diggelmann, (1984) *Mol. Cell. Biol.* 4:2929). The vectors were constructed from the respective fragments by standard methods. XbaI sites were added to the $V_L$ gene fragments of anti-Tac and 145-2C11 by PCR. The $V_L$ gene of anti-Tac was cloned in the gpt containing vector and the $V_L$ gene of 145-2C11 in the hyg containing vector to generate the respective plasmids pTAC-k and p145.2C11-k.

Transfection. Transfection was by electroporation using a Gene Pulser apparatus (Bio-Rad, Richmond, Calif.) at 360 V and 25 μFD capacitance according to the manufacturer's instructions. Before transfection, the light chain and heavy chain containing plasmids were linearized using FspI, extracted with phenol-chloroform, and ethanol precipitated. All transfections were done using 20 μg of each plasmid DNA and about $10^7$ Sp2/0 cells (ATCC CRL 1581) in phosphate-buffered saline (PBS). The cells from each transfection were plated into one 96-well tissue culture plate. After 48 hr, selective medium was applied: DMEM+10% fetal calf serum (FCS)+either HT media supplement (Sigma, St. Louis, Mo.) plus 300 μg/ml xanthine with 1 μg/ml mycophenolic acid or 500 μg/ml hygromycin (Boehringer Mannheim Biochemicals, Indianapolis, Ind.). After the wells had become confluent with surviving colonies of cells, medium from each well was assayed for the presence and quantity of secreted antibodies by ELISA using goat anti-mouse gamma Ig (Sigma).

Flow Cytometry. $2.5 \times 10^4$ Hut-102 cells were incubated with various concentrations of anti-Tac, anti-Tac-Jun, or bispecific F(ab'-zipper)$_2$ in 100 μl of PBS at 4° C. for 30 min. Cells were then washed in PBS, resuspended in 25 μl of PBS containing 50 ng of FITC-conjugated rat anti-mouse kappa (Pandex, Mundelein, Ill.), and incubated at 4° C. for 30 min. Cells were washed with PBS, fixed in 1% paraformaldehyde and analyzed by FACScan (Becton Dickinson, Mountain View, Calif.). The binding of anti-CD3 or its derivatives to EL4 cells was similarly analyzed. To estimate the concentration of bispecific F(ab'-zipper)$_2$, a standard curve of fluorescence intensity vs anti-CD3 antibody concentration was used.

F(ab'-zipper)$_2$ purification. Media supernatant from transfectants was passed over a column of monoclonal rat anti-mouse kappa Sepharose (Zymed, South San Francisco, Calif.), and bound proteins were eluted with 0.2M glycine-HCl, pH 2.1. The eluted fractions were neutralized with Tris base and dialyzed against PBS. In one experiment, concentrated medium from a supertransfectant was adjusted to pH 5.2 by 1:4 dilution in 10 mM MES buffer and was loaded onto a BAKERBOND ABx column (J. T. Baker, Phillsburg, N.J.) for separation on a FPLC system (Pharmacia LKB Biotechnology, Piscataway, N.J.). Bound proteins were eluted with a linear gradient of 0–0.25M $(NH_4)_2SO_4$, and F(ab'-zipper)$_2$ proteins were identified by ELISA or flow cytometry as described above. Bispecific F(ab'-zipper)$_2$ formed in vitro was similarly purified by ABx chromatography. F(ab'-zipper)$_2$ concentration in impure fractions was estimated by flow cytometry as described above. In pure protein fractions the concentration was determined by absorbance at 280 nm, assuming that 1 mg/ml has an $A_{280}$ of 1.4.

Formation of bispecific F(ab'-zipper) in vitro. Homodimers of anti-Tac-Jun and anti-CD3-Fos were reduced with 2-mercaptoethanylamine in PBS at 37° C. for 1 hr to form Fab'-zippers. They were then mixed and dialyzed against redox buffer (50 mM Tris-HCl, pH 8.5, 1 mM EDTA, 500 μM reduced glutathione and 500 μM oxidized glutathione) for 48 hr at 4° C., and the buffer was changed back to PBS by dialysis.

Cytotoxicity assay with mouse effector cells. Mouse spleen cells were cultured in DMEM+10% FCS+4 μg/ml Concanavalin A. After 3 days, the cells were passaged 1:2 in DMEM+10% FCS+10 U/ml recombinant IL-2 (Amgen, Thousand Oaks, Calif.). The effector cells were harvested 4 days later and used in the cytotoxicity assay. Target cells were prepared by incubating HuT-102 cells with 100 μCi $Na_2^{51}CrO_4$ (Amersham, Chicago, Ill.) in 100 μl of DMEM at 37° C. for 1 h. The cells were washed 2 times with DMEM before use. Cytotoxicity was measured by a standard $^{51}Cr$-release assay in a 96-well tissue culture plate. Each well received 50 μl of bispecific F(ab'-zipper )$_2$ in PBS, $10^4$ $_{51}$Cr-labeled HuT-102 cells in 50 μl of DMEM, and 50 μl of effector cells in DMEM. Total volume in each well was 200 μl. The cell mixtures were incubated at 37° C. for 4 h to allows lysis. After centrifugation, supernatant was removed from each well to assay for the release of $^{51}Cr$ from HuT-102 cells. Percentages of specific release in the cytotoxicity assay were calculated as: {Counts released by bispecific F(ab'-zipper)$_2$ minus counts released without added F(ab'-zipper)$_2$}/{Counts released by 0.1% SDS minus counts released without added F(ab'-zipper)$_2$}×100. All points in the cytotoxicity assay were determined in triplicate and their means were plotted.

Construction and transfection of Fab'-leucine zipper genes. We used the PCR method to join the Jun or Fos leucine zipper sequence to the first codon of the $C_H2$ exon of a mouse IgG2a gene (FIG. 1). At the fusion junctions, two glycine codons were introduced to make the joints more flexible in the protein products. After the leucine zipper sequences, a stop codon and a sequence containing the polyadenylation signal from the mouse IgG2a gene were included. The gene fusions were separately inserted into an expression vector previously used for heavy chain synthesis (FIG. 2). $V_H$ genes for desired antibodies can be inserted in the XbaI sites of the resulting new vectors. It is expected that mRNA transcripts will then initiate from the CMV promoter on each plasmid, and the $V_H$, $C_H1$, hinge and $C_H2$/leucine zipper exons will be spliced together.

In the Jun expression plasmid we inserted the $V_H$ gene of the mouse anti-Tac antibody, and in the Fos plasmid, the $V_H$ gene of the hamster 145-2C11 antibody. The anti-Tac antibody binds to the p55 chain of the human Il-2 receptor (IL-2R) (Uchiyama et al., (1981) *J. Immunol.* 126:1393); its heavy and light chain genes were previously cloned (Queen et al., (1989) *Proc. Natl. Acad. Sci. USA* 86:10029). The 145-2C11 antibody recognizes the ε chain of the mouse CD3 complex (Leo et al., (1987) *Proc. Natl. Acad. Sci. USA* 84:1374); its heavy and light chain genes were also cloned. Each $V_H$ gene included the signal sequences and J segment, and was followed by a splice donor sequence to allow splicing to the $C_H1$ domain (Queen et al., (1989) *Proc. Natl. Acad. Sci. USA* 86:10029). Analogous plasmids were prepared that respectively contained the $V_L$ genes of anti-Tac and 145-2C11 together with the mouse $V_K$ gene (FIG. 2).

Each heavy chain expression plasmid was cotransfected with the corresponding light chain plasmid into the murine myeloma cell line Sp2/0. Stable transfectants were selected using the gpt marker for anti-Tac-Jun, and the hyg marker for anti-CD3-Fos. Media supernatant from each transfectant was screened for the presence of antibody protein by ELISA with goat anti-mouse gamma antibody. ELISA-positive transfectants were confirmed by using flow cytometry to test their supernatants for the presence of antibody-like molecules binding to CD3 and p55 positive cell lines. In both cases, transfectants were obtained at a frequency of about 1 per $10^5$ myeloma cells. The transfectants secreted about 0.1–2 $\mu$g/ml/$10^6$ cells/24 h of F(ab')2-like molecule. The level of production of these molecules appears to be slightly lower than that of whole antibody molecules in similar experiments. The higher yielding transfectants for anti-Tac-Jun and anti-CD3-Fos were expanded for further characterization.

Figure 3:
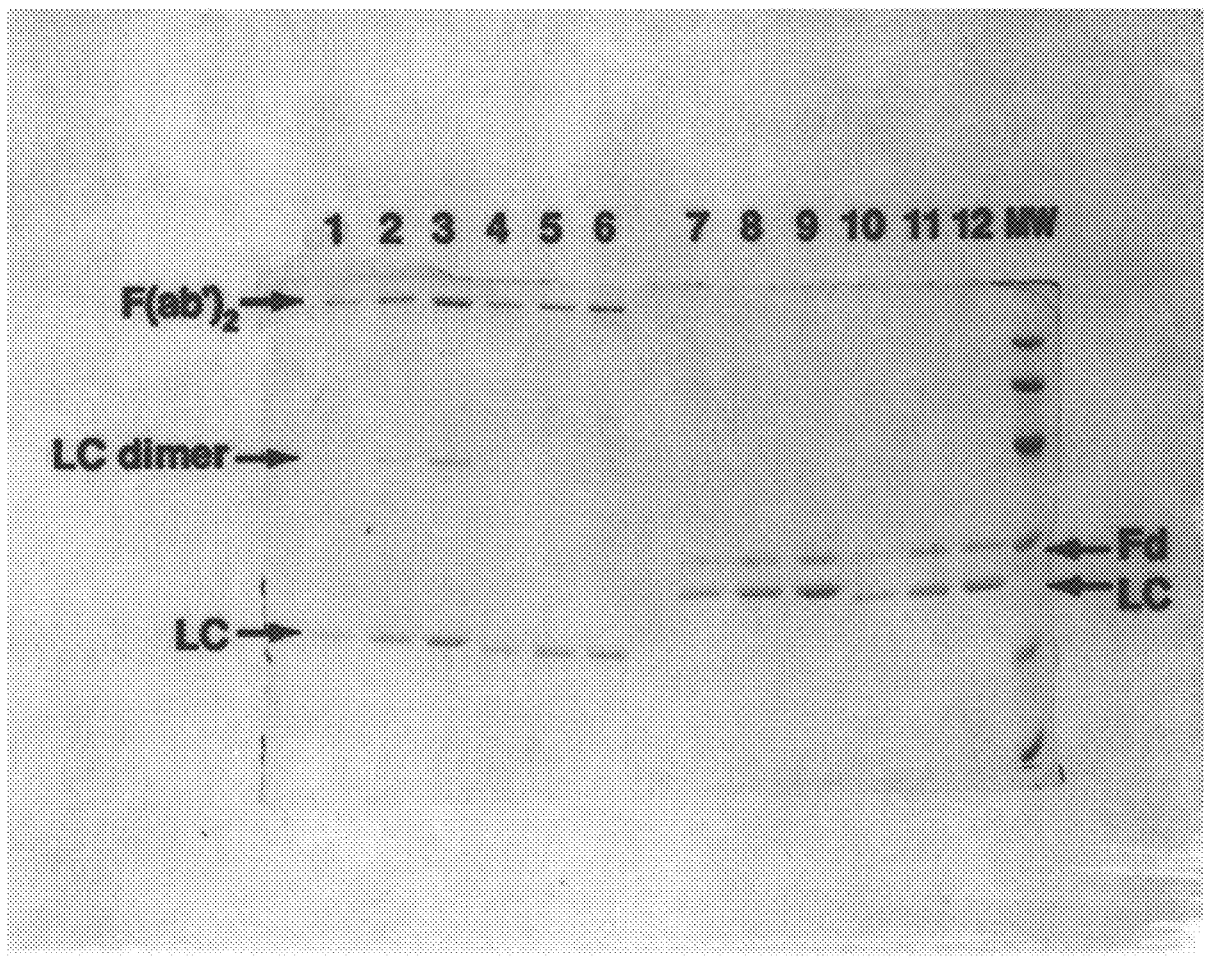
FIG. 3. SDS PAGE analysis of anti-Tac-Jun and anti-CD3-Fos purified by the rat anti-mouse kappa Sepharose. Proteins were analyzed on a 12.5% polyacrylamide gel and stained with coomassie blue. Lanes 1, 2, 3 are purified anti-CD3-Fos, and lanes 4, 5, 6 anti-Tac-Jun run under nonreducing conditions. Lanes 7, 8, 9 are anti-CD3-Fos and lanes 10, 11, 12 anti-Tac-Jun run under reducing conditions. M.W markers are: phosphorylase b, 94 kd; bovine serum albumin, 67 kd; ovalbumin, 43 kd; carbonic anhydrase, 30 kd; soy bean trypsin inhibitor, 20 kd; and lysozyme, 14 kd. Abbreviations are: F(ab')$_2$, F(ab'-zipper)$_2$; LC, light chain; and Fd, Fd-zipper.

Purification and characterization of anti-Tac-Jun and anti-CD3-Fos. Affinity chromatography was used to purify anti-Tac-Jun and anti-CD3-Fos. Supernatant from each kind of transfectant was loaded onto a rat anti-mouse kappa Sepharose column. Proteins that bound to the column were eluted with glycine-HCl at pH 2.1. After dialysis against PBS, the eluted proteins were analyzed on an SDS PAGE gel (Laemmli, (1970) *Nature* 227:680) with or without reduction (FIG. 3). The reduced proteins displayed only 2 bands, of apparent molecular weights 25 kd and 31 kd, corresponding respectively to the light chain and the heavy chain Fd-zipper. The nonreduced proteins displayed major bands of approximate molecular weights 25 kd or less and 100 kd or more. In light of the fact that both bands can be reduced to light chain and Fd-zipper, they most likely represent free light chain (25 kd), and F(ab'-zipper)$_2$ dimers of anti-Tac-Jun and anti-CD3-Fos. In addition, the anti-CD3-Fos sample contained a 50 kd band, which consisted of light chain dimers, as verified below. It should be mentioned that the affinity chromatography used to purify the proteins would capture free light chains and light chain dimers but not free Fd-zipper chains. So it is highly unlikely that this 50 kd protein is the Fd-zipper dimer. The influence of intrachain disulfide bonds on the mobility of the proteins on SDS PAGE can be observed by comparing the degree of light chain migration with or without reduction.

Formation of bispecific F(ab'-zipper)$_2$ in vivo. Having shown that the plasmid constructs could direct expression of appropriate F(ab'-zipper)$_2$ homodimers, we then showed that bispecific F(ab'-zipper)$_2$ could be produced in vivo by expressing all four different polypeptide chains needed for anti-Tac-Jun and anti-CD3-Fos in one transfectant. An anti-CD3-Fos transfectant was further transfected with the plasmid constructs for anti-Tac-Jun. Supertransfectants were selected using both the gpt and the hyg markers and screened by ELISA for secretion of antibody proteins that could bind to purified IL-2R p55. Supernatants from these supertransfectants were also analyzed by flow cytometry for the presence of anti-Tac as well as anti-CD3 activities.

A representative supertransfectant producing both anti-Tac and anti-CD3 activity was expanded to further characterize its antibody products. Media supernatant from this supertransfectant was analyzed by FPLC chromatography on an ABx column, eluting with a (NH$_4$)$_2$SO$_4$ gradient (FIG. 4A). only five peaks contained proteins reactive in an ELISA assay for mouse heavy and light chain were eluted (FIG. 4B). The antibody-positive peaks, designated as fractions I, II, III, IV, and V, were assayed by flow cytometry for binding to CD3$^+$ EL4 T-lymphoma cells and IL-2R$^+$ HuT-102 cells. Fraction II contained both anti-Tac and anti-CD3 activities, whereas fraction I contained mostly anti-Tac activity and fractions III and IV and V anti-CD3 activity only (FIG. 4C). In other experiments, media from transfectants separately expressing anti-Tac-Jun and anti-CD3-Fos was chromatographed in the same system: anti-Tac-Jun eluted in the same position as fraction I and anti-CD3-Fos in the position of fraction IV (data not shown). So fraction II contains bispecific antibody and fraction III and V other hybrid antibodies having only anti-CD3 activity.

Figure 5:
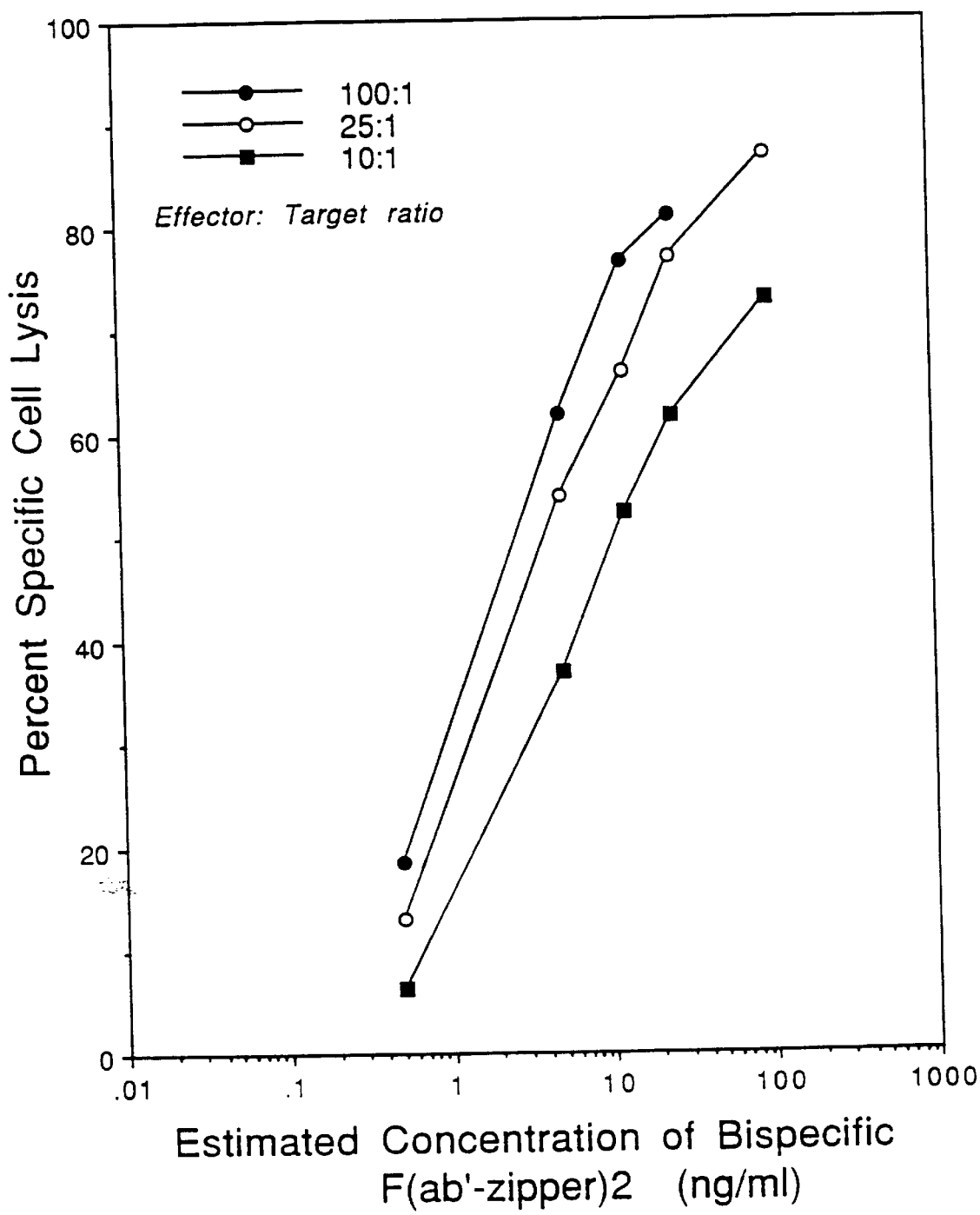
FIG. 5. Targeted cytotoxicity mediated by bispecific antibody from fraction II. Effectors and $^{51}$Cr-labeled target cells at ratios of 100:1 (●), 25:1 (○), and 10:1 (■) were incubated with various dilutions of fraction II (FIG. 4A) for specific lysis. Points represent means of triplicate determinations. Protein concentrations were estimated by flow cytometry.

To demonstrate that fraction II indeed contained bispecific activity, we used it to mediate the lysis of $^{51}$Cr-labeled HuT-102 cells by activated mouse splenic T cells (FIG. 5). Protein in fraction II would lyse the target cells down to a concentration below 20 ng/ml. Purified anti-CD3-Fos and anti-Tac-Jun homodimers, either alone or in combination, were totally ineffective in lysing the cells. These data indicate that bispecific activity could indeed be formed in vivo.

Figure 6:
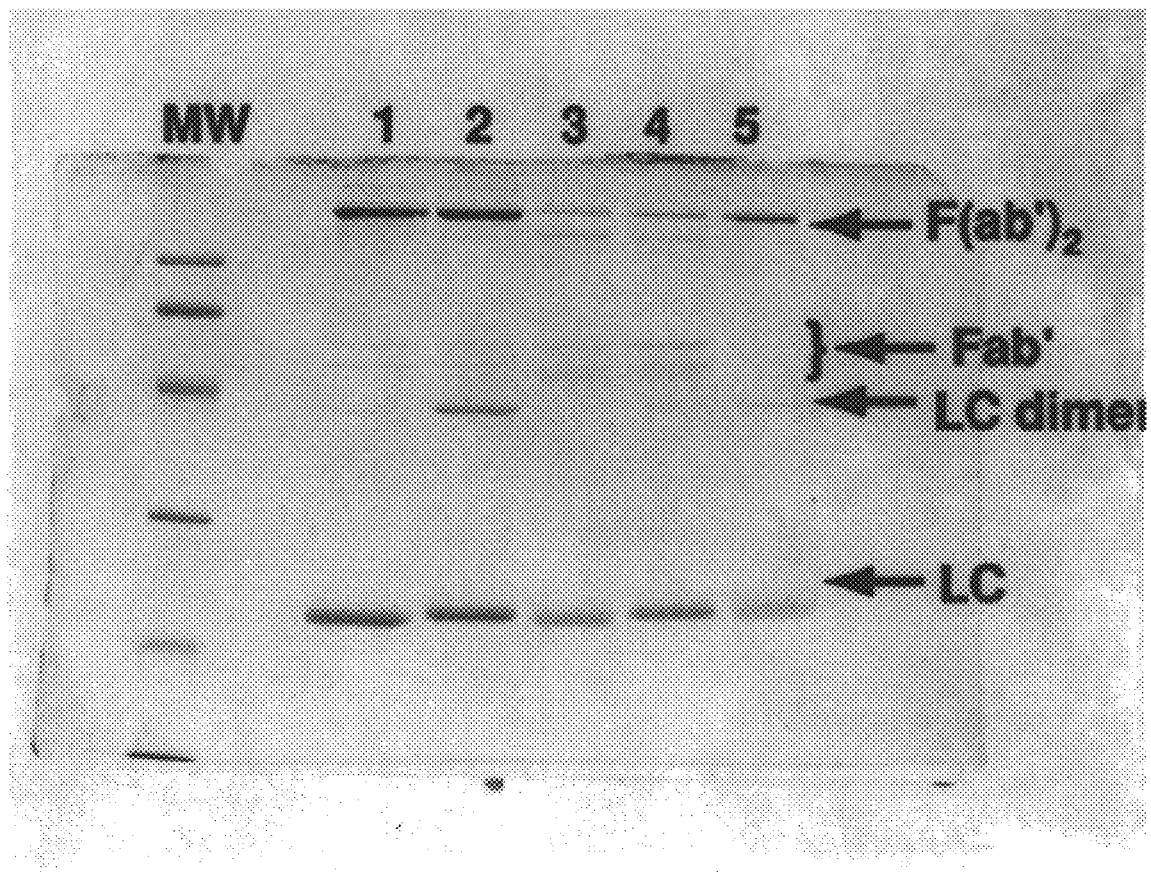
FIG. 6. Formation of bispecific F(ab'-zipper)$_2$ in vitro as analyzed by SDS PAGE under nonreducing conditions. Lane 1, anti-Tac-Jun prior to reduction; lane 3, anti-Tac-Jun after reduction with 4 mM 2-mercaptoethylamine; lane 4, anti-CD3-Fos after reduction with 2 mM 2-mercaptoethylamine and lane 5, anti-Tac-Jun x anti-CD3-Fos after dialysis against redox buffer. All protein samples were treated with 20 mM of iodoacetamide to block free sulfhydryls before boiling in sample SDS buffer. M.W. markers are the same as those used in FIG. 3. They were boiled in reducing sample SDS buffer before use. Abbreviations are: F(ab')$_2$, F(ab-zipper)$_2$; Fab', Fab'-zipper; and LC, light chain.

Formation of bispecific F(ab'-zipper)$_2$ in vitro. The homodimeric F(ab'-zipper)$_2$ proteins could be reduced at the hinge region to form Fab'-zipper monomers. Various concentrations of 2-mercaptoethylamine were used to determine the best conditions to form Fab'-zipper without the dissociation of light chain from the heavy chain Fd-zipper. The reduction products were analyzed on SDS PAGE under nonreducing conditions. The best conditions for the reduction of the purified anti-Tac-Jun was with 4 mM 2-mercaptoethylamine in PBS at 37° C. for 1 h. Anti-CD3-Fos required 2 mM 2-mercaptoethylamine under the same conditions. The proteins reduced under these conditions are shown in FIG. 6. In both cases a set of protein bands of 50–55 kd, corresponding to the Fab'-zipper, appeared upon reduction. The reason for the heterogeneity is unclear, but it has been observed before by others (Curran and Franza, (1988) *Cell* 55:395). The light chain dimer in the anti-CD3-Fos sample was also reduced into monomer very readily. Under these conditions there was minimum dissociation of the light chain from the Fab'-zipper, as evidenced by the absence of the Fd-zipper band (compare with FIG. 3).

Figures 7A, 7B:
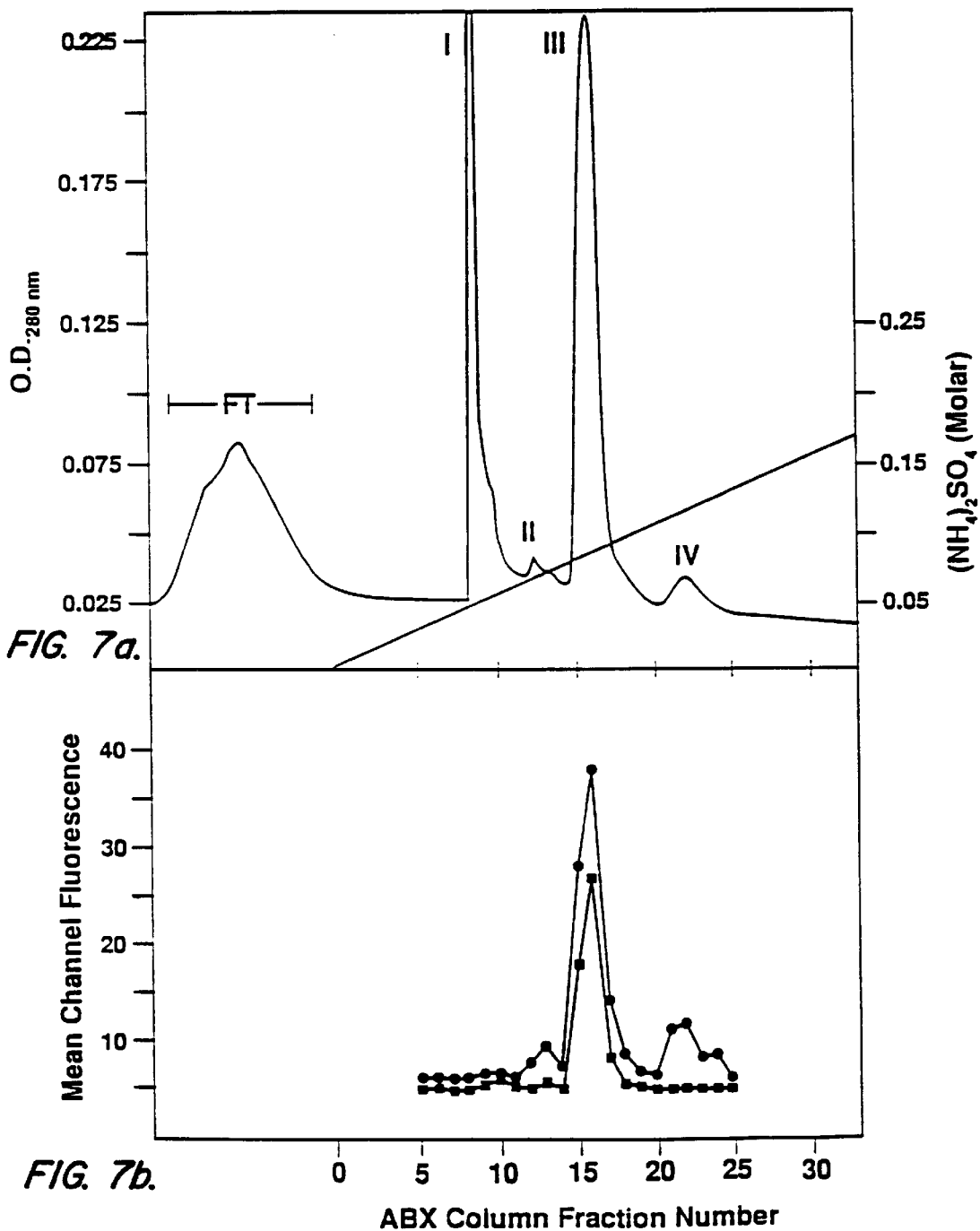
FIG. 7. Fractionation of the bispecific F(ab-zipper)$_2$ formed in vitro. Anti-Tac-Jun x anti-CD3-Fos formed in vitro was dialyzed against 10 mM MES buffer, pH 5.2 before loading onto a BAKERBOND ABx column. Proteins that were bound to the column were eluted by a gradient of $(NH_4)_2SO_4$. (A) Absorbance profile at 280 nm. (B) Anti-CD3 (●) and anti-Tac (■) activity for different fractions assayed by flow cytometry.
Figure 8A:
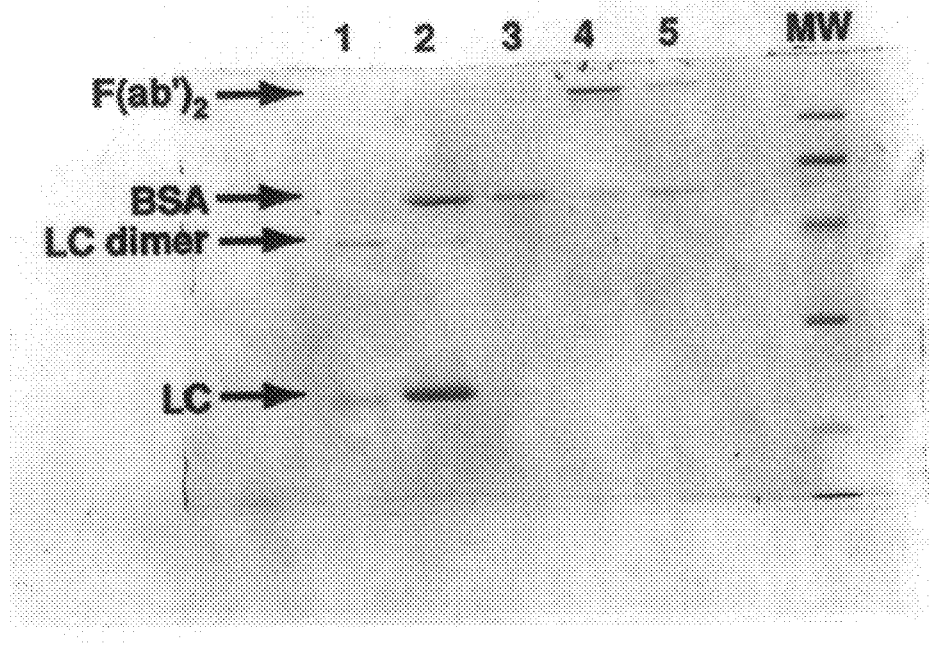
FIG. 8. SDS PAGE analyses of the peak fractions in FIG. 7 run under (A) nonreducing or (B) reducing conditions. Lane 1, the ABx column flow-through fraction; lane 2, fraction I; lane 3, fraction II; lane 4, fraction III; and lane 5, fraction IV. More volume (5-fold) was taken from fraction II and fraction IV for sampling. M.W. markers are the same as those used in FIG. 3. Abbreviations are: F(ab')$_2$ F(ab-zipper)$_2$; LC, light chain; and Fd, Fd-zipper.

The anti-Tac and anti-CD3 Fab'-zipper proteins were mixed together at a 1:1 ratio and a final concentration of 100 $\mu$g/ml, dialyzed against a redox buffer, and then dialyzed against PBS. The Fab'-zipper bands disappeared, and a new band corresponding to a F(ab'-zipper)$_2$ protein appeared (FIG. 6, lane 5). The new proteins were fractionated by ABx chromatography under the same conditions used for the F(ab'-zipper)$_2$ produced in vivo. There were three major and two minor protein peaks in the chromatogram (FIG. 7A). A combination of ELISA, flow cytometry (FIG. 7B), and SDS PAGE (FIG. 8) was used to identify the peaks. The flow through (FT) fraction contained excess light chains and light chain dimers only. The first eluted major peak (fraction I) contained mostly light chains but also a minor amount of anti-Tac-Jun detected by flow cytometry. In addition, this fraction, as well as the following fractions, contained BSA, which was used to pretreat the ABX column to prevent nonspecific protein sticking. The second eluted peak (fraction II) had minor amounts of both anti-Tac and anti-CD3 activities according to flow cytometry, and was composed of F(ab'-zipper)$_2$partly in aggregated forms. The last peak (fraction IV) was identified as anti-CD3-Fos because of its elution position (see fraction IV, FIG. 4A) and its EL4 cell binding activity.

Figure 8B:
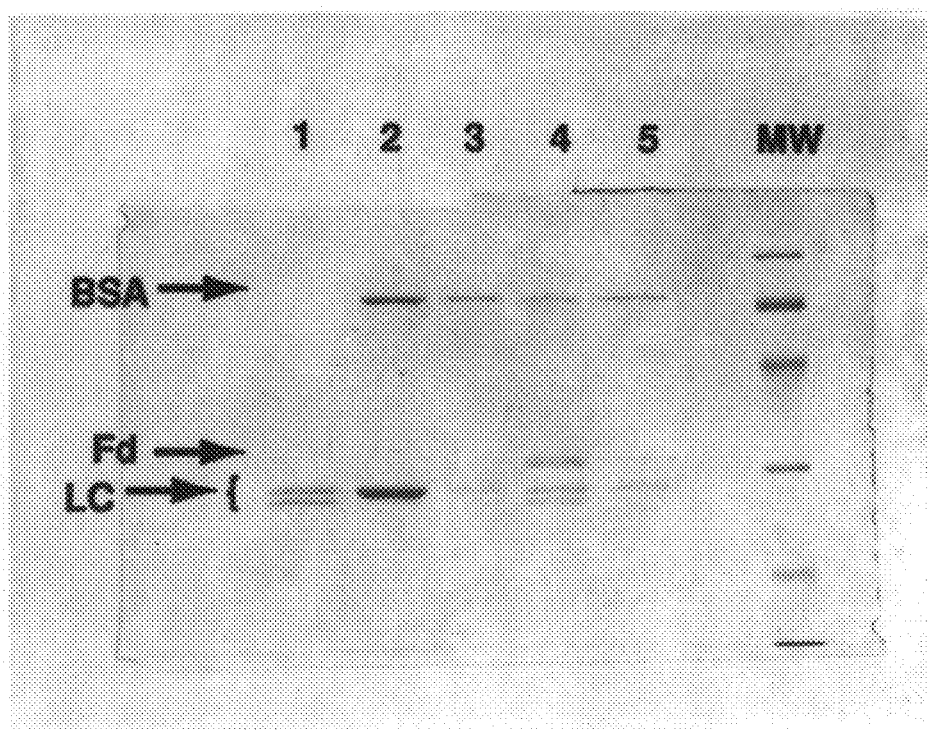

The third major peak (fraction III) on the chromatogram eluted precisely in the same position as the in vivo produced bispecific F(ab'-zipper)$_2$ (FIG. 4A, fraction II). This fraction binds to both CD3$^+$ EL4 cells and IL-2R$^+$ HuT-102 cells. only one principle protein band was observed on SDS PAGE of this fraction (FIG. 8A, lane 4), with the molecular weight expected for F(ab'-zipper)$_2$. Upon reduction, it dissociated into two closely migrating Fd-zipper bands and two distinct light chain bands in roughly equal amounts (FIG. 8B, lane 4). By running anti-CD3-Fos homodimers side by side with this sample, we were able to identify the upper Fd-zipper band as anti-CD3-Fos Fd-zipper and the upper light chain band as anti-CD3-Fos light chain (compare lane 4 and 5 in FIG. 8B). Because anti-Tac-Jun and anti-CD3-Fos homodimers were shown to elute in other fractions, fraction III must consist of heterodimers of anti-Tac-Jun with anti-CD3-Fos. To confirm that this fraction contains bispecific antibody, we used it for targeted killing of Hut-102 cells by mouse T cells. Specific lysis was seen at a concentration of less than 10 ng/ml (FIG. 9). Taken together, these data show that the F(ab'-zipper)$_2$ formed in vitro by disulfide exchange is mainly the bispecific anti-Tac x anti-CD3, with little side product formation.

From the foregoing, it will be appreciated that the bispecific antibodies of the present invention offer numerous advantages over other bispecific antibodies. In comparison to bispecific antibodies that are not formed by pairwise linkage of two leucine zippers, the present bispecific antibodies can be more economically produced in highly purity and yield. This improved purity and yield will permit bispecific antibodies that can be used for therapy of human or veterinary disease, or for prevention of disease.

Although the present invention has been described in some detail by way of illustration and example for purposes of clarity and understanding, it will be apparent that certain changes and modifications may be practiced within the scope of the appended claims.

---

What is claimed is:

1. A bispecific antibody, comprising:

a first protein comprising a first Fos or Jun leucine zipper linked to a first immunoglobulin having a $V_H$, $C_{H1}$, and hinge region and a light chain; and a second protein comprising a second Fos or Jun leucine zipper linked to a second immunoglobulin having a $V_H$, $C_{H1}$, and hinge region and a light chain, wherein said second protein is linked to said first protein by pairwise affinity of said second leucine zipper for said first leucine zipper and by disulfide-bonding between cysteine residues in the hinge reasons of the first and second proteins.

2. A bispecific antibody, comprising:

a first protein comprising a Fos leucine zipper linked to a first immunoglobulin having a $V_H$, $C_{H1}$, and hinge region and a light chain; and a second protein comprising a Jun leucine zipper linked to a second immunoglobulin having a $V_H$, $C_{H1}$, and hinge region and a light chain; wherein said second protein is linked to said first protein by pairwise affinity of said Fos leucine zipper for said Jun leucine zipper and by disulfide-bonding between cysteine residues in the hinge regions of the first and second proteins.

3. A bispecific antibody of claim 1, wherein said first leucine zipper has the amino acid sequence shown in SEQ. ID NO: 3 and said second leucine zipper has the amino acid sequence shown in SEO. ID NO: 5.

4. A bispecific antibody of claim 1, wherein the first immunoglobulin having a $V_H$, $C_{H1}$, and hinge region and a light chain binds to a human IL-2 receptor protein with an affinity of about $10^8$ $M^{-1}$ or greater.

5. A bispecific antibody of claim 1, wherein the second epitope binding immunoglobulin having a $V_H$, $C_{H1}$, and hinge region and a light chain binds to human CD3 protein with an affinity of about $10^8$ $M^{-1}$ or greater.

6. A bispecific antibody of claim 1, wherein the first immunoglobulin having a $V_H$, $C_{H1}$, and hinge region and a light chain is an Fab'.

7. A bispecific antibody of claim 1, wherein at least one said immunoglobulin having a $V_H$, $C_{H1}$, and hinge region and a light chain is a humanized immunoglobulin.

8. A bispecific antibody of claim 1, wherein said first and second leucine zippers comprise three, four, or five leucine zipper heptad motifs.

9. A bispecific antibody, comprising:

a first protein having a first Fos or Jun leucine zipper linked to a first Fab'; and a second protein having a second Fos or Jun leucine zipper linked to a second Fab', wherein said first protein is linked to said second protein by pairwise affinity of said second Fos or Jun leucine zipper for said first Fos or Jun leucine zipper and by disulfide bonding between cysteines residues in the hinge regions of the first and second Fab's.

10. A bispecific antibody of claim 9, wherein said first Fos or Jun leucine zipper is a Fos leucine zipper and said second Fos or Jun leucine zipper is a Jun leucine zipper.

11. A method for preparing bispecific antibodies, said method comprising:

producing a first protein comprising a first Fos or Jun leucine zipper linked to a first immunoglobulin having a $V_{H, CH1}$, and hinge region and a light chain capable of binding a first epitope;

producing a second protein comprising a second Fos or Jun leucine zipper joined to a second immunoglobulin having a $V_H$, $C_{H1}$, and hinge region and a light chain capable of binding a second epitope, wherein said second Fos or Jun leucine zipper has pairwise affinity for said first Fos or Jun leucine zipper; and contacting said first protein with said second protein in conditions that permit formation of a F(ab'-zipper)$_2$ heterodimer in which said first protein is linked to said second protein by pairwise affinity of said Fos leucine zipper for said Jun leucine zipper and by disulfide-bonding between cysteine residues in the hinge regions of the first and second proteins to form said bispecific antibody.

12. A method according to claim 11, wherein said first and second leucine zippers comprise three, four, or five leucine zipper heptad motifs.

13. A method according to claim 11, further comprising:

cleaving a covalent linkage between said first Fos or Jun leucine zipper and said first immunoglobulin having a $V_H$, $C_{H1}$, and hinge region and a light chain; and cleaving a covalent linkage between said second Fos or Jun leucine zipper and said second immunoglobulin having $V_H$, $C_{H1}$, and hinge region and a light chain to form a bispecific antibody comprising a heterodimer of a first immunoglobulin having $V_H$, $C_{H1}$, and hinge region and a light chain disulfide-bonded to a second immunoglobulin having $V_H$, $C_{H1}$, and hinge region and a light chain.

14. A method according to claim 13, further comprising a step of isolating the disulfide-bonded first and second immunoglobulins having $V_H$, $C_{H1}$, and hinge regions and light chains away from said cleaved first and second Fos or Jun leucine zippers.

15. A method according to claim 13, wherein cleavage of a Fos or Jun leucine zipper from an immunoglobulin having $V_H$, $C_{H1}$, and hinge region and a light chain occurs at a linkage comprising an asparagine-glycine peptide bond which can be cleaved by hydroxylamine.

16. The method of claim 13, further comprising formulating the bispecific antibody with a carrier to form a pharmaceutical composition.

* * * * *